(12) United States Patent
Wilzbach et al.

(10) Patent No.: US 11,036,039 B2
(45) Date of Patent: Jun. 15, 2021

(54) MICROSCOPY SYSTEM

(71) Applicant: Carl Zeiss Meditec AG, Jena (DE)

(72) Inventors: Marco Wilzbach, Stuttgart (DE);
Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 401 days.

(21) Appl. No.: 15/977,792

(22) Filed: May 11, 2018

(65) Prior Publication Data
US 2018/0348495 A1 Dec. 6, 2018

(30) Foreign Application Priority Data

May 11, 2017 (DE) ...................... 10 2017 208 019.1
Mar. 22, 2018 (DE) ...................... 10 2018 204 426.0

(51) Int. Cl.
G02B 21/16 (2006.01)
A61B 1/04 (2006.01)
(Continued)

(52) U.S. Cl.
CPC .............. G02B 21/16 (2013.01); A61B 1/043 (2013.01); G01N 21/6456 (2013.01);
(Continued)

(58) Field of Classification Search
CPC .... G02B 21/16; G02B 5/204; G02B 21/0012; G02B 2207/113; G01N 21/6458;
(Continued)

(56) References Cited

U.S. PATENT DOCUMENTS

2009/0202119 A1 8/2009 Hefti et al.
2011/0042580 A1* 2/2011 Wilson ............... G01N 21/6456
250/458.1
(Continued)

FOREIGN PATENT DOCUMENTS

DE 10 2015 011 429 A1 3/2017

OTHER PUBLICATIONS

P.A. Valdes et al., "A spectrally constrained dual-band normalization technique for protoporphyrin IX quantification in fluorescence-guided surgery", Optical Society of America, Optics Letter, vol. 37, Issue 11, pp. 1817-1819, Jun. 1, 2012.
(Continued)

Primary Examiner — Stephone B Allen
Assistant Examiner — Rahman Abdur
(74) Attorney, Agent, or Firm — Falk Ewers; Ewers IP Law PLLC

(57) ABSTRACT

A microscopy system has a detection system, which is configured to detect light of a first channel in a detection region and convert it to a first fluorescent light signal, to detect light of a second channel in a second detection region and convert it to a first correction signal, and to detect light of a third channel in a third detection region and convert it to a second correction signal. The system further includes a controller, which is configured to determine an approximation value for the spatial distribution of the concentration of the fluorescent dye in an object region using the first fluorescent light signal, the first correction signal, and the second correction signal. A first part of the emission spectrum of the fluorescent dye is detected in the first detection region.

23 Claims, 8 Drawing Sheets

(51) Int. Cl.
  *G02B 21/00* (2006.01)
  *G06T 7/00* (2017.01)
  *G02B 5/20* (2006.01)
  *G01N 21/64* (2006.01)

(52) U.S. Cl.
  CPC ......... *G01N 21/6458* (2013.01); *G02B 5/204* (2013.01); *G02B 21/0012* (2013.01); *G06T 7/0012* (2013.01); *G01N 2021/6419* (2013.01); *G01N 2021/6421* (2013.01); *G01N 2201/0636* (2013.01); *G02B 2207/113* (2013.01); *G06T 2207/10056* (2013.01); *G06T 2207/10064* (2013.01); *G06T 2207/30096* (2013.01)

(58) Field of Classification Search
  CPC ....... G01N 21/6456; G01N 2021/6421; G01N 2021/6419; G01N 2201/0636; G01N 2021/6439; G01N 21/6428; G06T 7/0012; G06T 2207/30096; G06T 2207/10064; G06T 2207/10056; A61B 1/043
  See application file for complete search history.

(56) References Cited

U.S. PATENT DOCUMENTS

2012/0300294 A1   11/2012  Jess et al.
2018/0180477 A1*  6/2018   Nieten ............... G01N 21/6458

OTHER PUBLICATIONS

German Office Action, with translation thereof, issued in German counterpart application No. DE 10 2017 208 019.1 dated Jan. 30, 2018.

* cited by examiner

MICROSCOPY SYSTEM

CROSS REFERENCE TO RELATED APPLICATIONS

This application claims priority to German patent application DE 10 2017 208 019.1, filed on May 11, 2017, and to German patent application DE 10 2018 204 426.0, filed Mar. 22, 2018, both of which are hereby incorporated by reference in their entireties.

TECHNICAL FIELD

The present disclosure relates to a microscopy system for simultaneously recording an overview image and for determining an approximation value for a spatial distribution of the concentration of a fluorescent dye.

BACKGROUND

Fluorescent dyes are used in the area of tumour resection to differentiate between diseased tissue and healthy tissue. To this end, a fluorescent dye is accumulated in the region of the diseased tissue, which, upon exposure to light of its excitation spectrum, emits fluorescent light of its emission spectrum. Since the fluorescent light comes only from the tissue in which the fluorescent dye has accumulated, additionally an overview image is helpful to be able to view the diseased image among the healthy tissue.

However, the fluorescent light emitted by the tissue is not a measure of the concentration of the fluorescent dye and consequently not a measure of the quantity/concentration of the diseased tissue, since the strength of the fluorescence also depends on other properties of the tissue. Tissue regions in which the same concentration of a fluorescent dye is present therefore appear with different intensities in fluorescence images, even though the concentration of the fluorescent dye is the same in these regions. The following properties of the tissue are responsible for the difference between the intensity that is emitted by the fluorescent dye and the intensity therefrom that arrives at a detector. First, the tissue absorbs light in the range of the excitation spectrum, and as a result not all the light provided for exciting the fluorescent dye actually reaches the fluorescent dye. In the emission wavelength range, light scattering of the fluorescent light has the effect that not all the light that is emitted by the fluorescent dye reaches the detector, but is scattered by the surrounding tissue.

It has been shown that a semi-empirical approximation for the light intensity that is actually emitted by a fluorescent dye exists which is dependent on the measured fluorescent light intensity and on the intensity of reflected light in the wavelength ranges of the absorption spectrum and the emission spectrum (P. A. Valdes et al., "A spectrally constrained dual-band normalization technique for protoporphyrin IX quantification in fluorescence-guided surgery," Optical Society of America, Optics Letter, Vol. 37, No. 11, Jun. 1, 2012, pp. 1817-1819).

A generalized approximation can be expressed as follows:

$$I_{FL}^{total} = A \frac{I_{FL}^{det}}{(I_{Ko1})^\alpha \cdot (I_{Ko2})^\beta},$$

wherein $I_{FL}^{tot}$ designates the spatial distribution of the intensity of fluorescent light which is emitted by the fluorescent dye without the disturbing influence of the surrounding tissue in the object region, $I_{FL}^{det}$ designates the spatial distribution of the intensity of fluorescent light which can be detected using a microscope and consequently contains the misrepresentations caused by the surrounding tissue, $I_{Ko1}$ designates the spatial distribution of the intensity of light of a wavelength range near the emission spectrum of the fluorescent dye that is reflected at the tissue, $I_{Ko2}$ designates the spatial distribution of the intensity of light of a wavelength range near the excitation spectrum of the fluorescent dye that is reflected at the tissue, A designates an empirical parameter, α designates a further empirical parameter, and β designates yet a further empirical parameter.

The parameters A, α, and β can be empirically determined, for example, using comparative methods. The spatial distributions of light intensities $I_{FL}^{det}$, $I_{Ko1}$, and $I_{Ko2}$ are therefore intensities of light of generally different wavelength ranges which are detected using a microscope. By contrast, $I_{FL}^{tot}$ designates the intensity distribution of light, which is actually produced by the fluorescent dye in the object region. In other words, the disturbing influence of the tissue surrounding the fluorescent dye is not reflected in $I_{FL}^{tot}$, but is reflected in $I_{FL}^{tot}$. Since $I_{FL}^{tot}$ represents the intensity distribution of fluorescent light without the disturbing influence of the tissue, $I_{FL}^{tot}$ is a measure of the spatial distribution of the concentration of the fluorescent dye in the object region and consequently also of the spatial distribution of the quantity/concentration of diseased tissue in the object region.

Conventional microscopy systems that are configured to detect $I_{FL}^{det}$, $I_{Ko1}$ and $I_{Ko2}$, have the disadvantage that these intensity distributions are detected sequentially one after the other, with the result that recording the intensity distributions $I_{FL}^{det}$, $I_{Ko1}$, and $I_{Ko2}$ is a lengthy process. This is a significant disadvantage especially in the field of surgery, because the tissue in the object region can change during the recording of said intensity distributions, which negatively influences the accuracy of the resulting intensity distribution $I_{FL}^{tot}$.

SUMMARY

It is therefore an objective of the present disclosure to provide a microscopy system that overcomes the above disadvantage. In particular, it is an object of the present disclosure to provide a microscopy system which repeatedly and quickly detects the spatial distribution of the concentration of a fluorescent dye.

The above objective is achieved by way of a microscopy system in accordance with the disclosure, which is configured to simultaneously record the intensity distributions $I_{FL}^{det}$, $I_{Ko1}$, and $I_{Ko2}$.

A microscopy system according to the disclosure for simultaneously recording an overview image and determining the concentration of a fluorescent dye in tissue in an object region comprises: a detection system which is configured to detect light of a first channel in a first detection region and convert it to a first fluorescent light signal, to detect light of a second channel in a second detection region and convert it to a first correction signal, and to detect light of a third channel in a third detection region and convert it to a second correction signal, wherein a first part of the emission spectrum of the fluorescent dye, i.e., a first emission wavelength range, is detected (substantially only) in the first detection region (first channel), wherein a wavelength range near the first part of the fluorescence spectrum, i.e., a first correction wavelength range, is detected (substantially only) in the second detection region (second channel), and wherein part of the excitation spectrum of the fluorescent dye, i.e., a second correction wavelength range, is detected (substantially only) in the third detection region (third channel).

"Substantially only" means that an optical unit of the microscopy system, which images onto the detection regions an object region in which tissue in which the fluorescent dye has accumulated can be situated, is configured such that at least 75%, typically at least 90%, more typically at least 99%, of light of the first emission wavelength range emanating from the object region is directed onto the first detection region, at least 75%, typically at least 90%, more typically at least 99%, of light of the first correction wavelength range emanating from the object region is directed onto the second detection region, and at least 75%, typically at least 90%, more typically at least 99%, of light of the second correction wavelength range emanating from the object region is directed onto the third detection region.

Alternatively, "substantially only" can be defined such that the ratio of the intensity of light of a specific wavelength at a detection region to the intensity of light of the same wavelength at a different detection region has a value of at least 10:1, typically at least 100:1, more typically at least 1000:1.

Hereby, the detection system provides three (image) signals which represent the spatial intensity distributions $I_{FL}^{det}$, $I_{Ko1}$, and $I_{Ko2}$. The microscopy system furthermore comprises a controller, which can determine the spatial distribution of the intensity of fluorescent light emitted in the object region and can determine therefrom an approximation value for the spatial distribution of the concentration of the fluorescent dye in the object region. For example, the approximation value is a value which is proportional to the concentration of the fluorescent dye in the object region.

Consequently, the controller is configured to eliminate the influence of the tissue that is arranged around the fluorescent dye from the signal $I_{FL}^{det}$. The resulting signal $I_{FL}^{tot}$ can be used by the controller to determine the spatial distribution of the concentration of the fluorescent dye in the object region.

In order to be able to separately detect the wavelength ranges on which the intensity distributions $I_{FL}^{det}$, $I_{Ko1}$ and $I_{Ko2}$ are based, the optical unit and/or the detection system can comprise different wavelength-dependent optical elements. These optical elements can comprise, for example, (dichroic) beam splitters, optical filters or filter matrices in the manner of a Bayer pattern.

The previously described microscopy system makes use of the fact that a relatively large wavelength range is situated between the (peak in the) absorption spectrum of a fluorescent dye and a (main) peak of the emission spectrum of the fluorescent dye, with the result that the first correction wavelength range and the second correction wavelength range do not, or substantially do not, overlap. The first correction wavelength range and the second correction wavelength range are therefore detected by different detection regions in different channels.

However, a fluorescent dye can have a plurality of local absorption maxima and a plurality of local emission maxima, or the wavelength range between the main absorption peak and the main emission peak can be small. In these cases, it may be advantageous to use the same detection region both for the first correction wavelength range and for the second correction wavelength range. In this case, the first correction wavelength range and the second correction wavelength range, spectrally speaking, are close together or overlap at least partially or significantly. Consequently, a single detection region can be used for detecting both the first correction wavelength range and the second correction wavelength range. Consequently, only one (single) correction signal is available for the determination of the approximation value for the spatial distribution of the concentration of the fluorescent dye. The other channels of a multichannel image detector, which also comprises the detection region in which the first and second correction wavelength ranges are detected, can therefore be used for recording an overview image. The microscopy system just described therefore takes advantage of a special case of the above-described expression for the approximation, for which is true that $I_{Ko1}$ can be considered an approximation for $I_{Ko2}$.

As a result, for this special case, a different function for determining the approximation value for the spatial distribution of the concentration of the fluorescent dye in the object region is obtained, wherein this function comprises as arguments the first fluorescent light signal and the first correction signal which represents light both of the first correction wavelength range and of the second correction wavelength range. In particular, this function can comprise as a term:

$$I_{FL}^{tot} = B \frac{I_{FL}^{det}}{(I_{Ko})^\gamma}$$

wherein
$I_{FL}^{tot}$ designates the spatial distribution of the intensity of fluorescent light emitted in the object region,
$I_{FL}^{det}$ designates the first fluorescent light signal,
$I_{Ko}$ designates the first correction signal,
B designates a parameter, and
γ designates a further parameter.

BRIEF DESCRIPTION OF THE DRAWINGS

The disclosure will now be described with reference to the drawings wherein.

DESCRIPTION OF EXEMPLARY EMBODIMENTS

Figure 1:
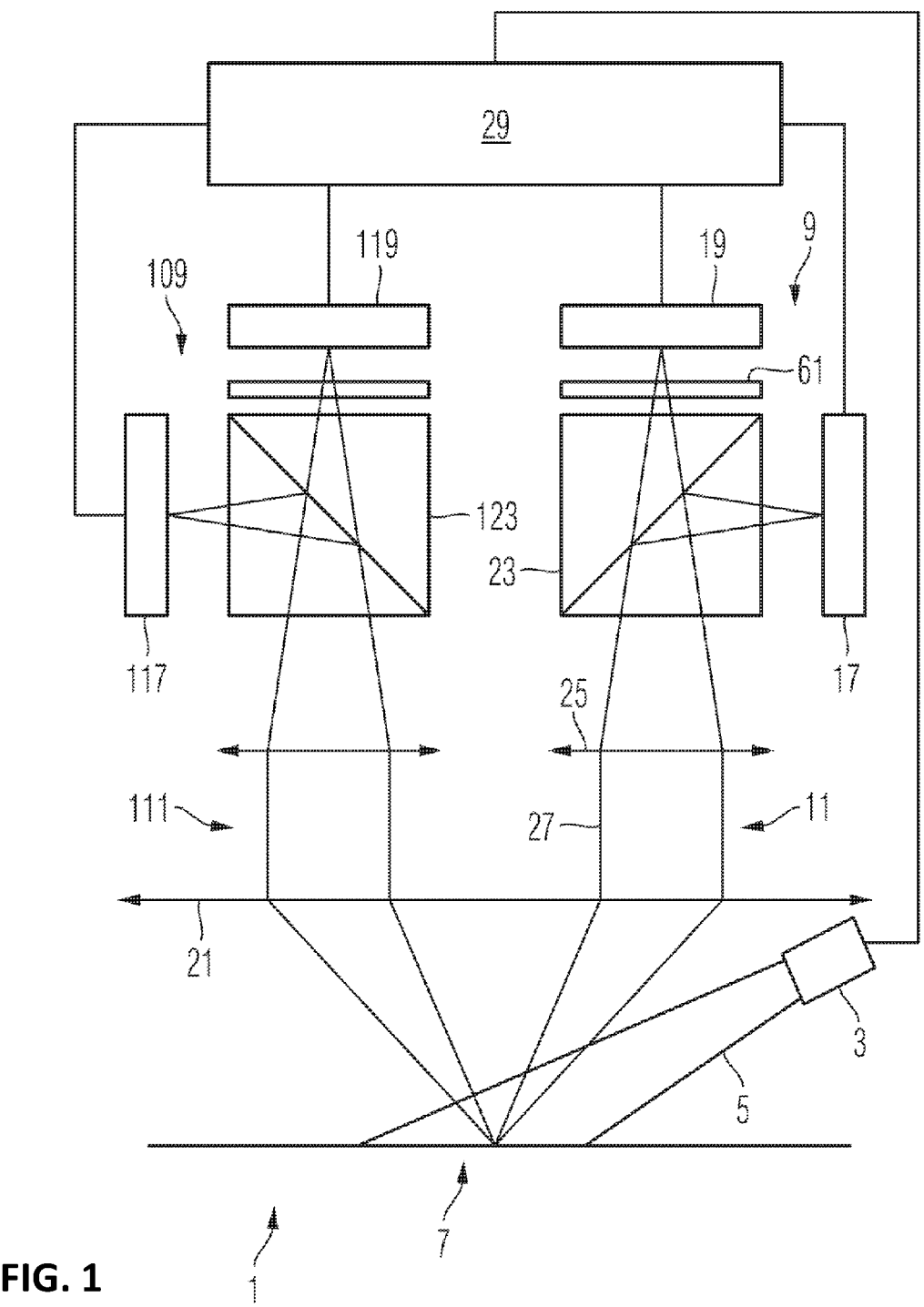
FIG. 1 shows a schematic illustration of a stereo microscope in accordance with an exemplary embodiment.

FIG. 1 shows a schematic illustration of a microscopy system 1 in accordance with an exemplary embodiment.

The microscopy system 1 comprises an illumination apparatus 3, which is configured to produce illumination light 5 and to direct it onto an object region 7. The illumination apparatus 3 can comprise one or more narrowband and/or broadband light sources and one or more illumination filters for producing the illumination light 5.

Arranged in the object region 7 can be for example tissue with a fluorescent dye. The fluorescent dye can be for example protoporphyrin IX (PPIX), which has an absorption spectrum (33) between approximately 350 nm and 650 nm, with the dominant absorption peak being at 405 nm, and having an emission spectrum (35) between 600 nm and 750 nm, with the dominant absorption peaks being at 635 nm and 705 nm (cf. diagram 31 in FIG. 2).

The microscopy system 1 furthermore comprises a first detection system 9 and a first optical unit 11.

The first detection system 9 comprises a first fluorescent light image detector 17 and a first multichannel image detector 19. The first fluorescent light image detector 17 is an image detector, i.e., the fluorescent light image detector 17 outputs a signal that represents an image, wherein the image represents the intensity of light that is incident on a detection region of the fluorescent light image detector 17 within a determined time period. Depending on the application, the first fluorescent light image detector 17 can be configured as a monochromatic sensor or as a multichannel image detector, wherein a multichannel image detector is suitable for detecting a plurality of different channels.

The first multichannel image detector 19 is likewise an image detector. A multichannel image detector has a plurality of different detection regions which can detect in each case light of one channel and output a signal for each channel. Here, "channel" designates a wavelength range. The channels at most partially spectrally overlap. For example, the channels of the first multichannel image detector overlap in pairs at most by 100 nm, typically at most by 50 nm. One example of a multichannel image detector is a conventional RGB color camera.

A conventional RGB color camera has the channels red (R), green (G), and blue (B). Here, the blue channel can comprise the wavelength range from 400 nm to 530 nm, the green channel can comprise the wavelength range from 460 nm to 600 nm, and the red channel can comprise the wavelength range from 570 nm to 750 nm.

The first optical unit 11 comprises an objective 21 and a first beam splitter 23. The first optical unit 11 can comprise further optical elements, for example the first image-forming lens 25 or a first zoom element (not illustrated in FIG. 1), which can be arranged between the first image-forming lens 25 and the objective 21.

The first optical unit 11 is configured to image the object region 7 onto detection regions of the first fluorescent light image detector 17 and the multichannel image detector 19, as is illustrated by way of a first beam path 27. The first optical unit 11 can comprise filters and filter matrices in the manner of a Bayer pattern, which are arranged directly in front of the detection regions. In other words, the optical unit here also comprises filters which are fixedly connected to the detectors.

The optical unit is configured to direct light of specific wavelengths substantially only onto a single one of the detection regions (depending on the stereo beam path).

Figure 2:
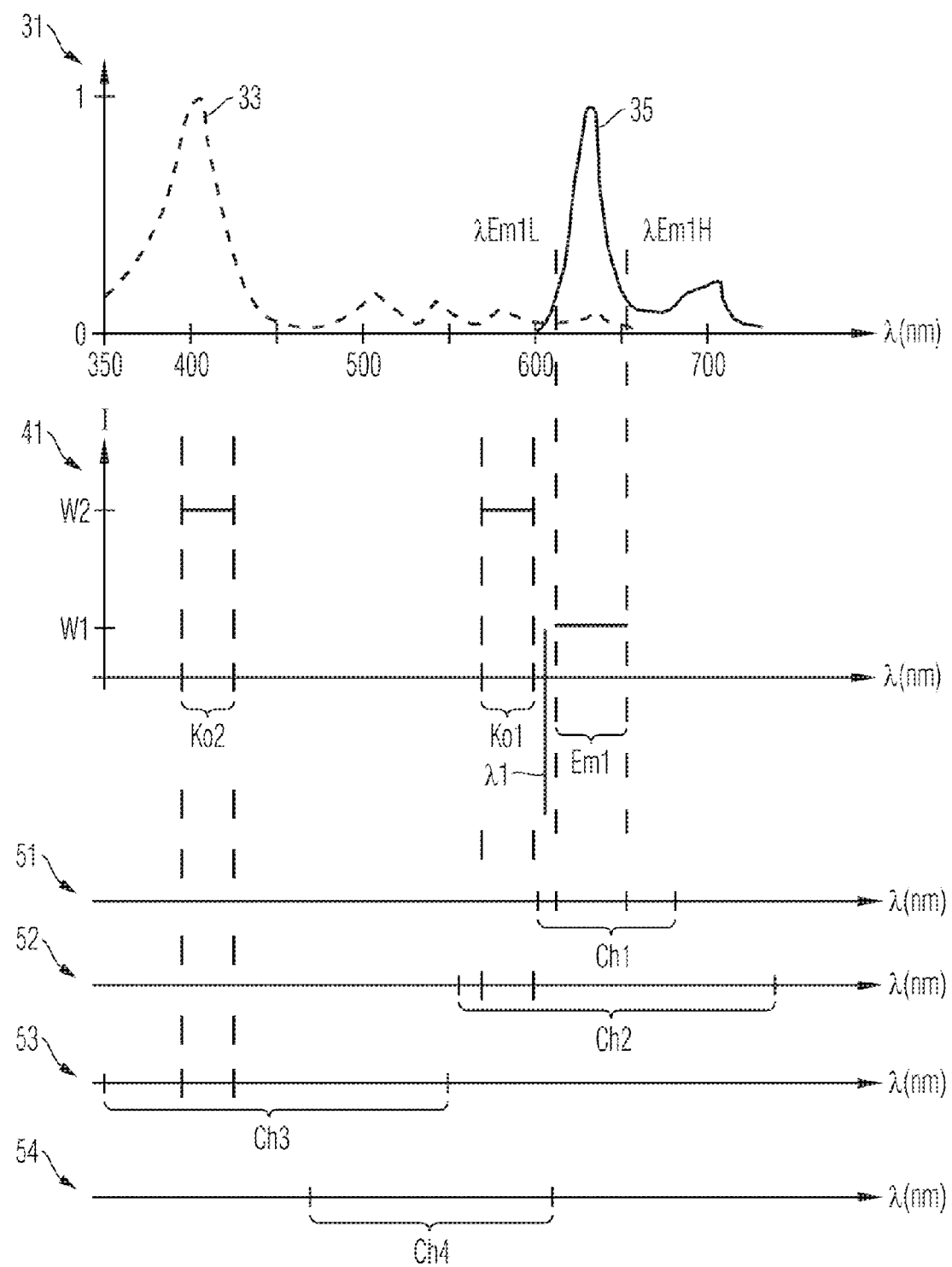
FIG. 2 shows an exemplary embodiment of a spectral configuration of elements of the stereo microscope of FIG. 1.

FIG. 2 shows a spectral configuration of the illumination light 5, of the first fluorescent light image detector 17, of the first multichannel image detector 19 and of the first beam splitter 23 for an exemplary fluorescent dye that is arranged in the object region 7.

Diagram 31 shows a normalized absorption spectrum 33 (normalized to its maximum value) and a normalized emission spectrum 35 (normalized to its maximum value). The absorption spectrum 33 and the emission spectrum 35 correspond to those of the fluorescent dye PPIX.

Diagram 41 shows the intensity of the illumination light 5 in dependence on the wavelength. In a first emission wavelength range Em1, which extends from λEm1L to λEm1H, the illumination light 5 has at most one first intensity W1. That is to say, within the entire wavelength range from λEm1L to λEm1H, the illumination light 5 does not at any wavelength have an intensity that is greater than the first intensity W1. The first emission wavelength range Em1 comprises at least a first part of the emission spectrum 35. In the first part of the emission spectrum, the normalized emission (normalized to the maximum value of the emission spectrum 35) has for example a value of at least 1%, typically at least 5%, more typically at least 10%.

A first correction wavelength range Ko1 is situated spectrally near the first emission wavelength range Em1. For example, the first correction wavelength range Ko1 is situated in the range between λEm1L−150 nm and λEm1H+150 nm. The first correction wavelength range Ko1 does not overlap the first emission wavelength range Em1. Within the first correction wavelength range Ko1, the illumination light 5 has at least a second intensity W2. That is to say within the entire correction wavelength range Ko1, the illumination light 5 does not at any wavelength have an intensity that is lower than the second intensity. The first intensity W1 is lower than the second intensity W2 for example by at least a factor of 2, 5, 10, 20, 50, 100, 1,000 or 10,000, as a result of which the object region 7 is exposed with light of the first correction wavelength range Ko1, while the first emission wavelength range Em1 is substantially not exposed.

A second correction wavelength range Ko2 comprises a first part of the excitation spectrum 33 of the fluorescent dye. The first part of the excitation spectrum 33 has for example a normalized absorption (normalized to the maximum value of the absorption spectrum 33) of at least 1%, typically at least 5%, more typically at least 10%. Within the second correction wavelength range Ko2, the illumination light 5 has at least the second intensity W2. That is to say within the entire correction wavelength range Ko2, the illumination light 5 does not at any wavelength have an intensity that is lower than the second intensity. The fluorescent dye is excited hereby, as a result of which the fluorescent dye emits light in the emission spectrum 35.

In the example shown in FIG. 2, the first emission wavelength range Em1 extends from 610 nm to 655 nm; the first correction wavelength range Ko1 extends from 560 nm to 595 nm; and the second correction wavelength range Ko2 extends from 390 nm to 420 nm. Alternatively, the first emission wavelength range Em1 can extend from 640 nm to 710 nm; the second correction wavelength range Ko2 can extend from 430 nm to 450 nm.

The first beam splitter 23 of the first optical unit 11 can be a dichroic beam splitter, for example. That means that the first beam splitter 23 can be configured to output light of a wavelength that is greater than a first limit wavelength $\lambda 1$ substantially only to the first fluorescent light image detector 17, and to output light of a wavelength that is smaller than the first limit wavelength $\lambda 1$ substantially only to the first multichannel image detector 19. "Substantially only" means, for example, that the ratio of the average transmittance in a first output (to the first fluorescent light image detector 17) in the wavelength range above the first limit wavelength $\lambda 1$ to the average transmittance in a second output (to the first multichannel image detector 19) in the same wavelength range is at least 100, typically at least 1000, more typically at least 10 000.

As in the example shown in FIG. 2, the first limit wavelength $\lambda 1$ can be situated between the first emission wavelength range Em1 and the first correction wavelength range Ko1. In the example shown in FIG. 2, the first limit wavelength is 600 nm. Light of the first emission wavelength range Em1 emanating from the object region 7 is hereby output (substantially only) to the first fluorescent light image detector 17. Light of the first correction wavelength range Ko1 emanating from the object region 7 is output (substantially only) to the first multichannel image detector 19; and light of the second correction wavelength range Ko2 emanating from the object region 7 is output (substantially only) to the first multichannel image detector 19.

It is also possible to use, instead of a dichroic beam splitter, a conventional beam splitter together with corresponding filters to achieve the same effect. A filter arranged between the conventional beam splitter and the first fluorescent light image detector 17 to this end has a high transmittance for example only in the first emission wavelength range Em1. A filter arranged between the conventional beam splitter and the first multichannel image detector 19 to this end has in each case a high transmittance for example in the first and second correction wavelength ranges and a low transmittance in the first emission wavelength range Em1. A ratio between a high and a low transmittance can be, for example, at least 100, typically at least 1,000, even more typically at least 10,000.

With the beam splitter 23 and further filters that spectrally separate the second and third channels from one another, the first optical unit 11 is configured to simultaneously image light of the first emission wavelength range Em1 emanating from the object region 7 onto a first detection region of the first fluorescent light image detector 17, light of the first correction wavelength range Ko1 emanating from the object region 7 onto a second detection region of the first multichannel image detector 19, and light of the second correction wavelength range Ko2 emanating from the object region 7 onto a third detection region of the first multichannel image detector 19. The further filters are for example those that have a conventional RGB color camera.

The first fluorescent light image detector 17 is configured to detect light of a first channel in the first detection region. Light of the first channel is detected in the first detection region and converted to a first fluorescent light signal. In other words, "channel" designates the wavelength range for which the first detection region of the first fluorescent light image detector 17 has a non-negligible sensitivity for light. The fluorescent light signal output by the first fluorescent light image detector 17 therefore represents the intensity of light of the first channel that is incident on the first detection region within a predetermined time period.

Diagram 51 illustrates the first channel Ch1. The first channel Ch1 comprises the first emission wavelength range Em1. The first detection region is therefore used to detect light of the first emission wavelength range Em1 and to output a corresponding signal, the fluorescent light signal. In the present example, the first channel Ch1 extends from approximately 600 nm to 670 nm.

The first multichannel image detector 19 is configured to detect light of a second channel Ch2 in a second detection region and to convert it to a first correction signal. Diagram 52 illustrates the second channel Ch2 of the first multichannel image detector 19. The second channel Ch2 comprises the first correction wavelength range Ko1. In the present exemplary embodiment, the second channel Ch2 extends from approximately 550 nm to over 700 nm. This approximately corresponds to the red channel of a conventional RGB color camera.

The first multichannel image detector 19 is furthermore configured to detect light of a third channel Ch3 in a third detection region and to convert it to a second correction signal. Diagram 53 illustrates the third channel Ch3 of the first multichannel image detector 19. The third channel Ch3 comprises the second correction wavelength range Ko2. In the present exemplary embodiment, the third channel Ch3 extends from approximately 350 nm to 540 nm. This approximately corresponds to the blue channel of a conventional RGB color camera.

Once again with reference to FIG. 1, the microscopy system 1 furthermore comprises a controller 29, which receives the first fluorescent light signal, the first correction signal and the second correction signal from the first fluorescent light image detector 17 and from the first multichannel image detector 19. The controller is configured to process the first fluorescent light signal, the first correction signal and the second correction signal and to determine therefrom an approximation value for the spatial distribution of the concentration of the fluorescent dye in the object region 7.

Due to the simultaneous and substantially exclusive imaging of the first emission wavelength range Em1 onto the first detection region, of the first correction wavelength range Ko1 onto the second detection region, and of the second correction wavelength range Ko2 onto the third detection region, it is possible to obtain signals for these three wavelength ranges at the same time. It is hereby possible to repeatedly quickly calculate the approximation value for the concentration of the fluorescent dye in the object region 7.

Further exemplary embodiments, which are based on the exemplary embodiments described in connection with FIGS. 1 and 2, will be described below.

According to a further exemplary embodiment, the optical unit 11 furthermore comprises a first optical filter 61 (cf. FIG. 1), which is arranged between the first beam splitter 23 and the first multichannel image detector 19. An average transmittance of the first optical filter 61 in the first correction wavelength range Ko1 can be at least 50%, typically at least 80%, more typically at least 90%. Furthermore, an average transmittance of the first optical filter 61 in the second correction wavelength range Ko2 can be at least 50%, typically at least 80%, more typically at least 90%. Furthermore, an average transmittance of the first optical filter 61 between the first correction wavelength range Ko1 and the second correction wavelength range Ko2 can be at most 30%, typically at most 10%, more typically at most 1%.

FIGS. 3A to 3D illustrate various exemplary embodiments for the illumination and for the first optical filter 61.

Figure 3A:
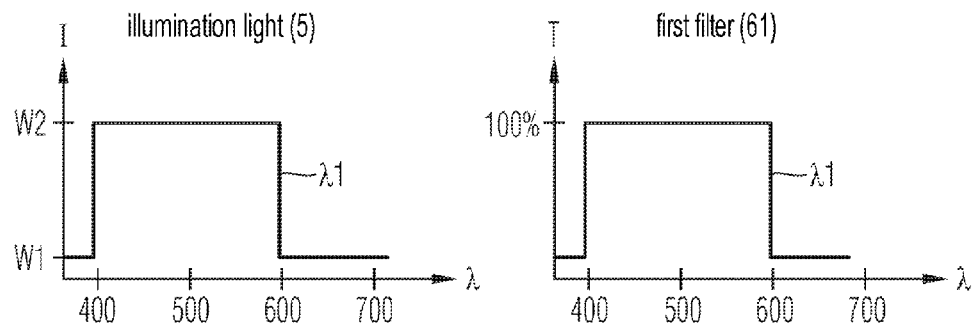
FIG. 3A shows an exemplary embodiment of a spectral configuration for illumination light for an optical filter of the stereo microscope of FIG. 1.

In the exemplary embodiment in accordance with FIG. 3A, the illumination light 5 has at least the second intensity W2 in the wavelength range of approximately 400 nm to approximately 600 nm, wherein the first limit wavelength λ1 of the dichroic beam splitter 23 is at approximately 600 nm. Outside this wavelength range, the illumination light 5 has at most the first intensity W1, i.e., from 600 nm to at least 720 nm. The wavelength range from 400 nm to 600 nm here comprises the first and second correction wavelength ranges.

The first optical filter 61 has a high average transmittance T in a wavelength range from approximately 400 nm to approximately 600 nm and has a low transmittance outside said wavelength range. For example, an average transmittance of the first optical filter (61) between 400 nm and 600 nm is at least 50%, typically at least 80%, more typically at least 90%. Hereby, the object region 7 is exposed in the first and second correction wavelength ranges, and the light of the first and second correction wavelength ranges that is reflected at the object region 7 is imaged onto the first multichannel image detector 19 by way of the first filter 61. Here, the reflected light is detected by the second detection region and the third detection region in different channels, to be precise in the second and in the third channel.

The first emission wavelength range Em1 can in this exemplary embodiment comprise for example a region around 635 nm, a region around 705 nm or a range from 635 nm to 705 nm. An average transmittance of the first optical filter (61) can have, in the first emission wavelength range (Em1), at most a value (W3) that is smaller than the average transmittance of the first optical filter (61) in the first correction wavelength range (Ko1) and/or second correction wavelength range (Ko2) by at least a factor of 10, typically 100, more typically 1,000.

As a result, for example if the first multichannel image detector 19 is a conventional RGB color camera, an overview image with high color fidelity can be recorded with the RGB camera, and in addition, the signal of the red channel, which comprises the first correction wavelength range Ko1, and the signal of the blue channel, which comprises the second correction wavelength range Ko2, can be used to determine the spatial distribution of the concentration of the fluorescent dye. While it is possible hereby to produce an overview image of particularly high color fidelity, the signal of the red channel represents not only the intensity of light of the first correction wavelength range Ko1, but also light of other wavelengths within the red channel. The same is correspondingly true for the blue channel. This can have a negative influence on the accuracy of the determination of the spatial distribution of the concentration of the fluorescent dye.

Figure 3B:
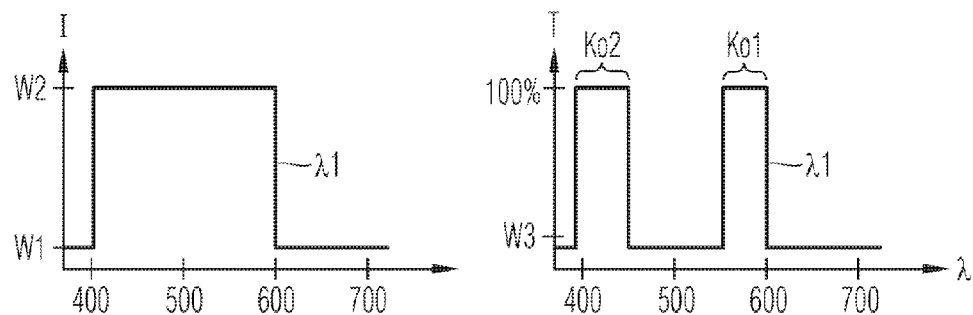
FIG. 3B shows another exemplary embodiment of a spectral configuration for illumination light for another optical filter of the stereo microscope of FIG. 1.

As illustrated in FIG. 3B, the illumination light 5 in accordance with a further exemplary embodiment corresponds to the illumination light 5, as is used in the exemplary embodiment shown in FIG. 3A. The first filter 61 in accordance with FIG. 3B has a high transmittance only in the first correction wavelength range Ko1 and in the second correction wavelength range Ko2 and, for the rest, has a low transmittance. For example, an average transmittance of the first optical filter (61) has, between the first correction wavelength range (Ko1) and the second correction wavelength range (Ko2), at most a value (W3) that is smaller than the average transmittance of the first optical filter (61) in the first correction wavelength range (Ko1) and/or second correction wavelength range (Ko2) by at least a factor of 10, 100, or 1,000. The ranges having high transmittances in the first filter 61 in accordance with FIG. 3B can also be wider in every direction than the first or second correction wavelength range by approximately 5 nm to 25 nm.

The overview image which is obtained in this exemplary embodiment using a conventional RGB camera (for the first multichannel image detector 19) does not exhibit color fidelity due to the suppression of a portion of the visible spectrum. However, the accuracy for the determination of the spatial distribution of the concentration of the fluorescent dye is improved because only light of the first correction wavelength range Ko1 is fed to the second detection region (red channel) and because only light of the second correction wavelength range Ko2 is fed to the third detection region (blue channel).

Figure 3C:
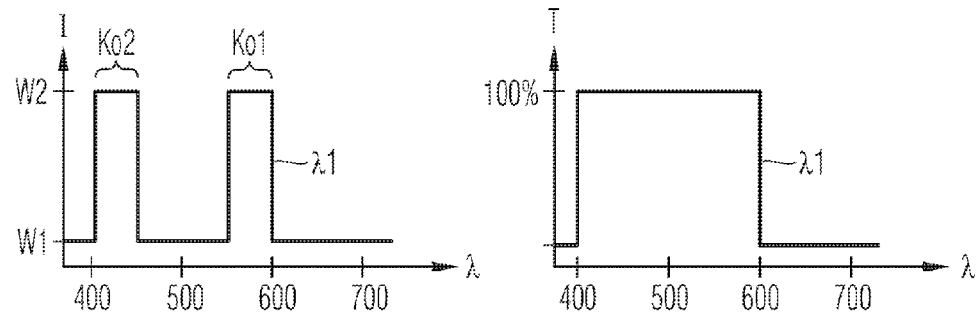
FIG. 3C shows another exemplary embodiment of a spectral configuration for illumination light for another optical filter of the stereo microscope of FIG. 1.

The same effect is also achieved by way of the exemplary embodiment illustrated in FIG. 3C. Here, the illumination light 5 has at least the second intensity W2 only in the first correction wavelength range Ko1 and in the second correction wavelength range Ko2, and for the rest has only at most the first intensity W1. The first filter 61 in accordance with FIG. 2C corresponds to the first filter 61 in accordance with FIG. 3A.

Figure 3D:
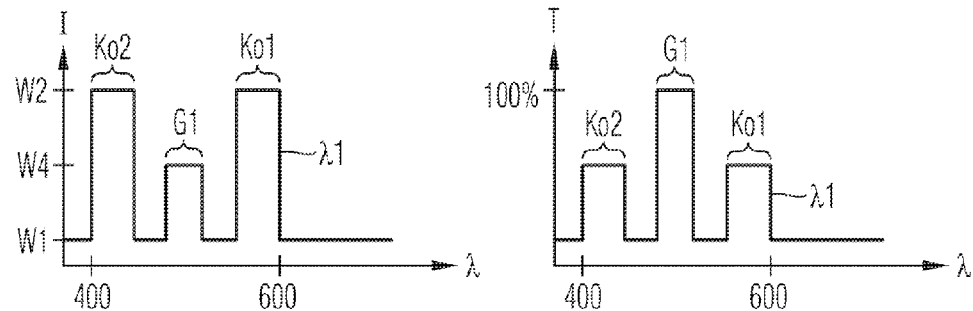
FIG. 3D shows another exemplary embodiment of a spectral configuration for illumination light for another optical filter of the stereo microscope of FIG. 1.

Improved color fidelity and at the same time a high degree of accuracy in the determination of the spatial distribution of the concentration of the fluorescent dye can be achieved with the configuration in accordance with FIG. 3D. To this end, the first multichannel image detector 19 furthermore has a fourth detection region, with which light of a fourth channel Ch4 can be detected and converted into a signal of the fourth channel. The fourth channel Ch4 at most partially overlaps the second and third channel, respectively. In a conventional RGB color camera, the fourth channel for example corresponds to the green channel, which is illustrated by way of example in FIG. 2 in diagram 54.

The illumination light 5 has, in a supplementary wavelength range G1, which is contained in the fourth channel Ch4 (green channel), an average fourth intensity W4. The average fourth intensity can be 0.01% to 50% of the second intensity (W2), typically 0.05% to 10% of the second intensity (W2), more typically 0.1% to 1% of the second intensity (W2). Here, the first intensity (W1) can be lower than the average fourth intensity (W4) by at least the factor of 10, typically by at least a factor of 100, more typically by at least a factor of 1,000.

The illumination light 5 can have for example at most the first intensity W1 between the first correction wavelength range Ko1 and the supplementary wavelength range G1 and between the supplementary wavelength range G1 and the second correction wavelength range Ko2. The supplementary wavelength range G1 can comprise, for example, a wavelength range of 520 nm to 570 nm.

An average transmittance of the first optical filter (61) is, in the first correction wavelength range (Ko1) and the second correction wavelength range (Ko2), for example in each case 0.01% to 50% of an average transmittance of the first optical filter (61) in the supplementary wavelength range (G1), typically 0.05% to 10% of the average transmittance of the first optical filter (61) in the supplementary wavelength range (G1), more typically 0.1% to 1% of the average transmittance of the first optical filter (61) in the supplementary wavelength range (G1).

An average transmittance of the first optical filter (61) can be, between the first correction wavelength range (Ko1) and the supplementary wavelength range (G1) and between the supplementary wavelength range (G1) and the second correction wavelength range (Ko2), lower than the average transmittance of the first optical filter (61) in the first correction wavelength range (Ko1) and/or second correction wavelength range (Ko2) by at least a factor of 10, typically 100, more typically 1,000.

In accordance with a further exemplary embodiment, the microscopy system 1 is a stereo microscopy system, as illustrated in FIG. 1. As such, the microscopy system 1 illustrated in FIG. 1 furthermore comprises a second detection system 109 and a second optical unit 111. The second detection system 109 can be configured to be similar or identical to the first detection system 9. The second optical unit 111 can be configured to be similar or identical to the first optical unit 11.

The second detection system 109 comprises a second fluorescent light image detector 117 and a second multichannel image detector 119. The second fluorescent light image detector 117 can be configured to be similar or identical to the first fluorescent light image detector 17. The second multichannel image detector 119 can be configured to be similar or identical to the first multichannel image detector 19.

If the second detection system 109 and the first detection system 9 have identical configuration, they each have the same spectral configuration.

Alternatively, the second fluorescent light image detector 117 and the second multichannel image detector 119 can have a different spectral configuration, with the result that a further emission wavelength range can be detected.

Here, the second fluorescent light image detector 117 is configured to detect a second emission wavelength range Em2, which differs from the first emission wavelength range Em1. The second emission wavelength range Em2 extends from $\lambda$Em2L to $\lambda$Em2H and is a second part of the emission spectrum 35 of the fluorescent dye. The first emission wavelength range Em1 and the second emission wavelength range Em2 can, for example, partially overlap or not overlap. For example, the first emission wavelength range Em1 and the second emission wavelength range Em2 can overlap by at most 50 nm, in particular, at most 20 nm or at most 10 nm.

The second fluorescent light image detector 117 is configured to detect light of a fifth channel in a fifth detection region and to convert it to a second fluorescent light signal. The second multichannel image detector 119 is furthermore configured to detect light of a sixth channel in a sixth detection region and to convert it to a third correction signal. The multichannel image detector 119 is furthermore configured to detect light of a seventh channel in a seventh detection region and to convert it to a fourth correction signal.

Figure 4:
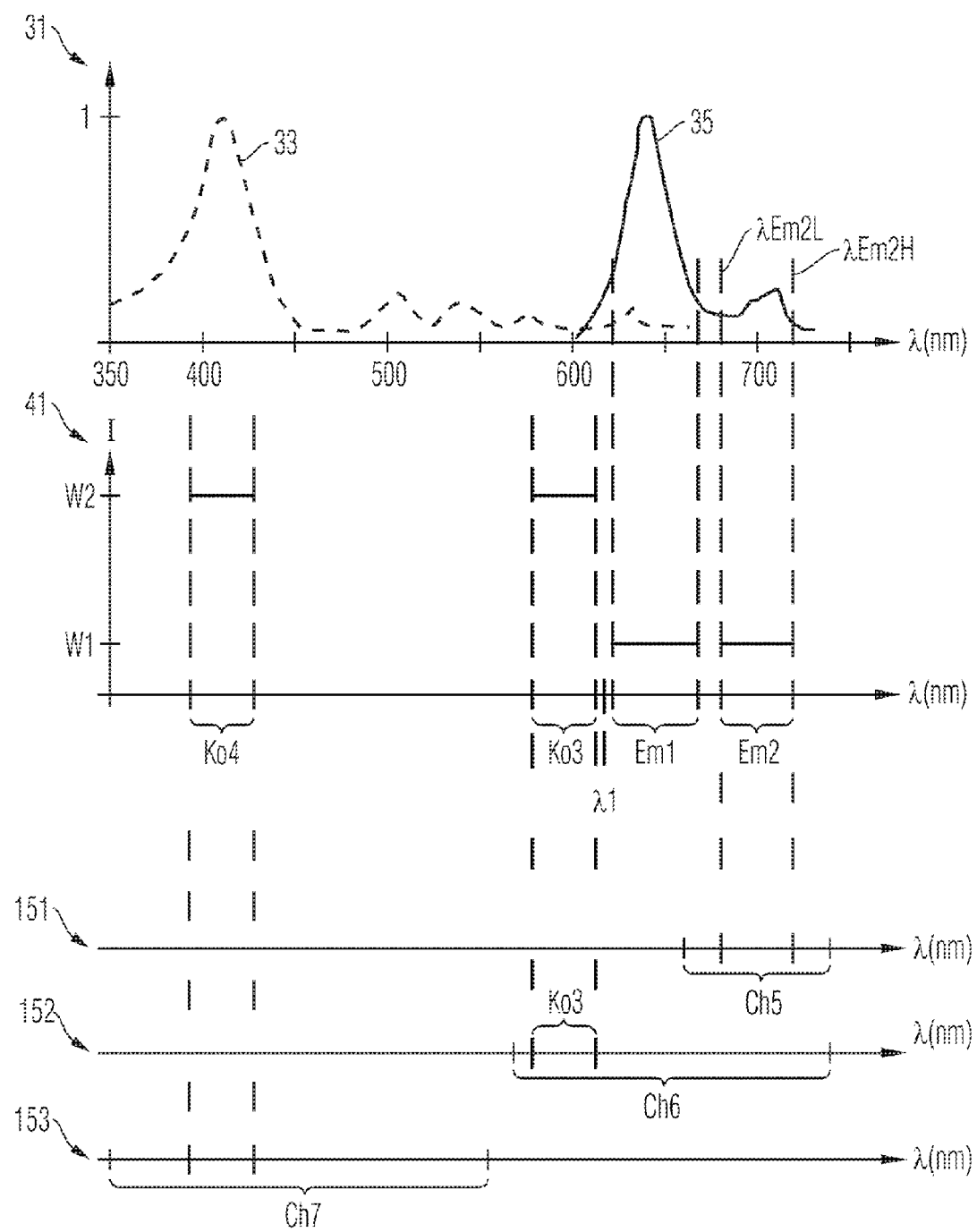
FIG. 4 shows an exemplary embodiment of a spectral configuration for illumination light and further elements of the stereo microscope of FIG. 1.

An exemplary embodiment of such an exemplary spectral configuration is represented in FIG. 4.

Diagram 31 shows the normalized absorption spectrum 33 and the normalized emission spectrum 35. Diagram 41 shows the intensity of the illumination light 5 in dependence on the wavelength.

Diagram 151 illustrates the fifth channel Ch5. The fifth channel Ch5 comprises the second emission wavelength range Em2. The fifth detection region is therefore used to detect light of the second emission wavelength range Em2 and to output a corresponding signal. In the present exemplary embodiment, the second emission wavelength range Em2 comprises a wavelength from 680 nm to 720 nm. In particular, the second emission wavelength range Em2 comprises the wavelength 705 nm.

Diagram 152 illustrates the sixth channel Ch6 of the second multichannel image detector 119. The sixth channel Ch6 comprises a third correction wavelength range Ko3. The third correction wavelength range Ko3 is situated between $\lambda$Em2L−150 nm and $\lambda$Em2H+150 nm and does not overlap the second emission wavelength range Em2. In the present exemplary embodiment, the sixth channel Ch6 extends from approximately 550 nm to over 700 nm. This approximately corresponds to the red channel of a conventional RGB color camera.

Diagram 153 illustrates the seventh channel Ch7 of the second multichannel image detector 119. The seventh channel Ch7 comprises a fourth correction wavelength range Ko4. The fourth correction wavelength range Ko4 comprises a second part of the excitation spectrum 33 of the fluorescent dye. In the present exemplary embodiment, the seventh channel Ch7 extends from approximately 350 nm to 540 nm. This approximately corresponds to the blue channel of a conventional RGB color camera.

Consequently, different parts of the emission spectrum can be detected separately from one another by different detectors, specifically the first and second fluorescent light image detectors.

The illumination light 5 has at most the first intensity W1 in the second emission wavelength range Em2. Furthermore, the illumination light 5 has at least the second intensity in the third correction wavelength range Ko3 and in the fourth correction wavelength range Ko4.

The second optical unit 111, which comprises the objective 21 and a second beam splitter 123, is configured to image light of the second emission wavelength range Em2 emanating from the object region (substantially only) onto the fifth detection region, to image light of the third correction wavelength range Ko3 emanating from the object region (substantially only) onto the sixth detection region, and to image light of the fourth correction wavelength range Ko4 emanating from the object region (substantially only) onto the seventh detection region. In particular, the second beam splitter 123 can be a dichroic beam splitter having a second limit wavelength $\lambda 2$ or be configured like the first beam splitter 23.

The controller 29 is furthermore configured to determine the approximation value for the spatial distribution of the concentration of the fluorescent dye in the object region 7 using furthermore the second fluorescent light signal, the third correction signal and the fourth correction signal.

Figure 5:
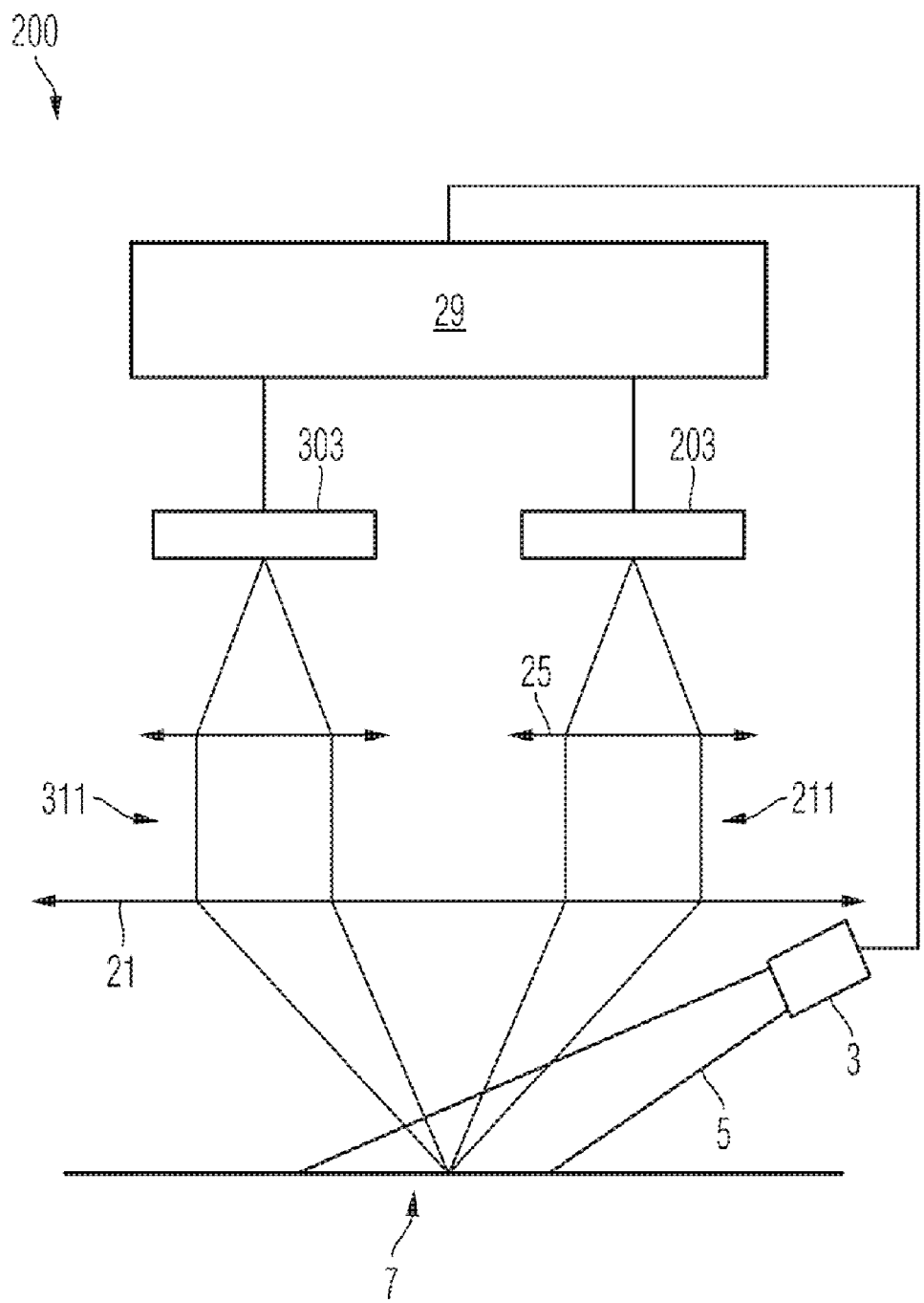
FIG. 5 shows a schematic illustration of a stereo microscope in accordance with a further exemplary embodiment.

FIG. 5 shows a further exemplary embodiment of a microscopy system 200 for simultaneously recording an overview image and determining the concentration of a fluorescent dye in tissue in an object region.

Components of the microscopy system 200, which are identical to those of the microscopy system 1 shown in FIG. 1, have been denoted with the same reference signs, and reference is made to their description.

The microscopy system 200 comprises the illumination apparatus 3, which is configured to produce illumination light 5 and to direct it onto the object region 7.

The microscopy system 200 comprises a first optical unit 211, which comprises an objective 21 and is configured to image light emanating from the object region 7 onto a first multichannel image detector 203. The first optical unit 211 can comprise an image-forming lens 25, as is shown in FIG. 5. The first optical unit 211 can furthermore comprise a zoom system (not illustrated).

The first multichannel image detector 203 is configured to detect light of a first channel Ch1 in a first detection region D1 and to convert it to a first fluorescent light signal, to detect light of a second channel Ch2 in a second detection region D2 and to convert it to a first correction signal, and to detect light of a third channel Ch3 in a third detection region D3 and to convert it to a second correction signal. The channels of the first multichannel image detector 203 substantially do not spectrally overlap, with the result that each of the detection regions substantially exclusively detects the channel it is assigned. In this way, different spectral ranges can be detected at the same time.

For two adjoining or partially overlapping channels M and N, for example the following condition may apply:

$$\int_{M \cup N} S_M(\lambda) \cdot S_N(\lambda) d\lambda \le W$$

wherein
$S_M$ represents the sensitivity of the detection region for the channel M which has been normalized to the maximum sensitivity,
$S_N$ represents the sensitivity of the detection region for the channel N which has been normalized to the maximum sensitivity,
$\lambda$ represents the wavelength, and
W is 20%, typically 10%, more typically 1%.

Figures 6, 7:
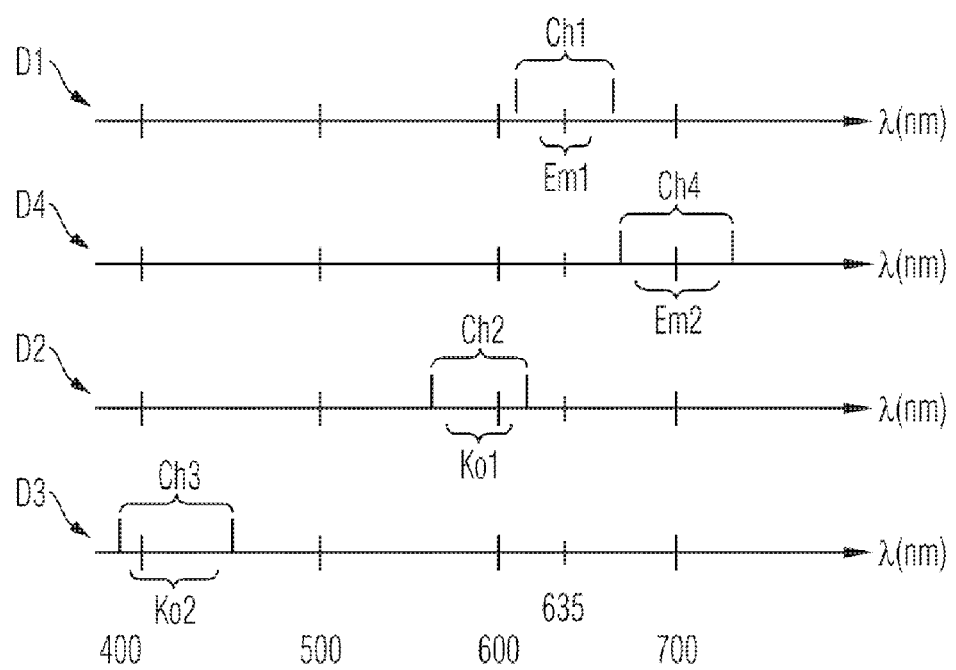
FIG. 6 shows a spatial configuration of detection regions of a multichannel image detector.
FIG. 7 shows an exemplary embodiment of a spectral configuration of detection regions of the stereo microscope of FIG. 5.

An exemplary embodiment of the configuration of the first multichannel image detector 203 is illustrated in FIGS. 6 and 7. FIG. 6 shows an exemplary embodiment of a spatial arrangement of the detection regions D1, D2, D3, and D4 of the first multichannel image detector 203. In this exemplary embodiment, the first multichannel image detector 203 has a further, fourth detection region D4 with which the first multichannel image detector 203 is configured to detect light of a fourth channel Ch4 and to output a corresponding signal. The first detection region D1 consists of a multiplicity of regularly arranged pixels. The second detection region D2, the third detection region D3 and the fourth detection region D4 likewise each consist of regularly arranged pixels, wherein the different detection regions do not spatially overlay one another.

FIG. 7 shows the channels of the first multichannel image detector 203. In other words, FIG. 7 shows as channels those wavelength ranges in which the respective detection regions have a significant sensitivity for light. A sensitivity can, for example, be considered to be significant for a specific wavelength if the sensitivity at this wavelength is at least 10%, typically at least 30% of the maximum sensitivity of the detection region.

In the present exemplary embodiment, the first detection region D1 is configured to detect light in a wavelength region around 635 nm (first channel Ch1). In particular, the first channel Ch1 comprises a wavelength range from 610 nm to 650 nm.

The fourth detection region D4 is configured to detect light of a wavelength region around 705 nm (fourth channel Ch4). In particular, the fourth channel comprises a wavelength range from 650 nm to 720 nm.

The second detection region D2 is configured to detect light of a wavelength region around 600 nm (second channel Ch2). In particular, the second channel Ch2 comprises a wavelength range from 560 nm to 610 nm.

The third detection region D3 is configured to detect light of a wavelength region around 405 nm (third channel Ch3). In particular, the third channel Ch3 comprises a wavelength range from 390 nm to 450 nm.

The spectral configuration of the individual detection regions can be achieved, for example, by bandpass filters, the production of which is known to a person skilled in the art.

Again with reference to FIG. 5, the illumination apparatus 3 is configured to produce the illumination light 5 such that it has at most a first intensity W1 in a first emission wavelength range Em1, which is part of the emission spectrum 35 of the fluorescent dye (cf. FIG. 2) and is contained in the first channel Ch1. The first emission wavelength range Em1 extends from λEm1L to λEm1H.

Furthermore, the illumination light 5 has at least a second intensity W2 in a first correction wavelength range Ko1 and in a second correction wavelength range Ko2. The first correction wavelength range Ko1 is contained in the second channel Ch2; and the second correction wavelength range Ko2 is contained in the third channel Ch3. The first correction wavelength range Ko1 is situated near the first emission wavelength range Em1, for example between λEm1L−150 nm and λEm1+150 nm and does not overlap the first emission wavelength range Em1. The second correction wavelength range Ko2 comprises a part of the excitation spectrum of the fluorescent dye. The first intensity W1 is lower than the second intensity W2 by at least a factor of 2. This is illustrated by way of example in diagram 41 of FIG. 2.

The microscopy system 200 furthermore comprises a controller 29, which is configured to determine an approximation value for the spatial distribution of the concentration of the fluorescent dye in the object region 7 using the first fluorescent light signal, the first correction signal and the second correction signal.

As illustrated in FIGS. 6 and 7, the first multichannel image detector 203 has the fourth detection region D4, which is configured to detect light of the fourth channel Ch4. The fourth channel can be selected for example such that it comprises a second emission wavelength range Em2, which is a second part of the emission spectrum of the fluorescent dye and does not overlap the first emission wavelength range. In this way it is possible to sample the emission spectrum in a plurality of different wavelength ranges, and a plurality of fluorescent light signals are then available for determining the approximation value for the spatial distribution of the concentration of the fluorescent dye. For example, the second emission wavelength range Em2 can comprise a wavelength range from 670 nm to 710 nm and can comprise in particular the wavelength 705 nm.

Alternatively, the fourth channel Ch4 can be configured to detect a wavelength range situated in the visible spectral range outside the emission spectrum (35) of the fluorescent dye, outside the second channel Ch2 and outside the third channel Ch3 in order to improve hereby the color fidelity of the overview image. For example, the fourth channel Ch4 can comprise a wavelength region around 500 nm to detect a wavelength range of green light.

As a further alternative, the multichannel image detector 203 can be configured such that the first channel Ch1 and the fourth channel Ch4 spectrally partially overlap. In this way it is also possible for the first emission wavelength range Em1 and the second emission wavelength range Em2 to spectrally partially overlap. The overlap between the first emission wavelength range Em1 and the second emission wavelength range Em2 can be, for example, at most 50 nm, in particular at most 20 nm or at most 10 nm. The overlap between the first channel Ch1 and the fourth channel can be, for example, at most 100 nm, in particular at most 50 nm or at most 20 nm.

As illustrated in FIG. 5, the microscopy system 200 can be in the form of a stereo microscopy system. Here, the microscopy system 200 furthermore has a second optical unit 311, which is configured to image the object region 7 onto a second multichannel image detector 303. The second multichannel image detector 303 can be configured to be similar or identical to the first multichannel image detector 203.

A further exemplary embodiment will be described below with reference to FIGS. 1, 8 and 9. The microscopy system in accordance with this exemplary embodiment substantially corresponds to the microscopy system 1 shown in FIG. 1, wherein the illumination light 5, the first optical unit 11, the second optical unit 111 and the first detection system 9 and the second detection system 109 have a different spectral configuration, which is illustrated in FIGS. 8 and 9.

The microscopy system 1 comprises a first detection system 9, which comprises a first fluorescent light image detector 17 and a first multichannel image detector 19. The first fluorescent light image detector 17 is configured to detect light of a first channel Ch1 in a first detection region and to convert it to a first fluorescent light signal. The first multichannel image detector 19 is configured to detect light of a second channel Ch2 in a second detection region and to convert it to a first correction signal.

The illumination apparatus 3 is configured to produce illumination light 5 and to direct it onto the object region 7.

Figure 8:
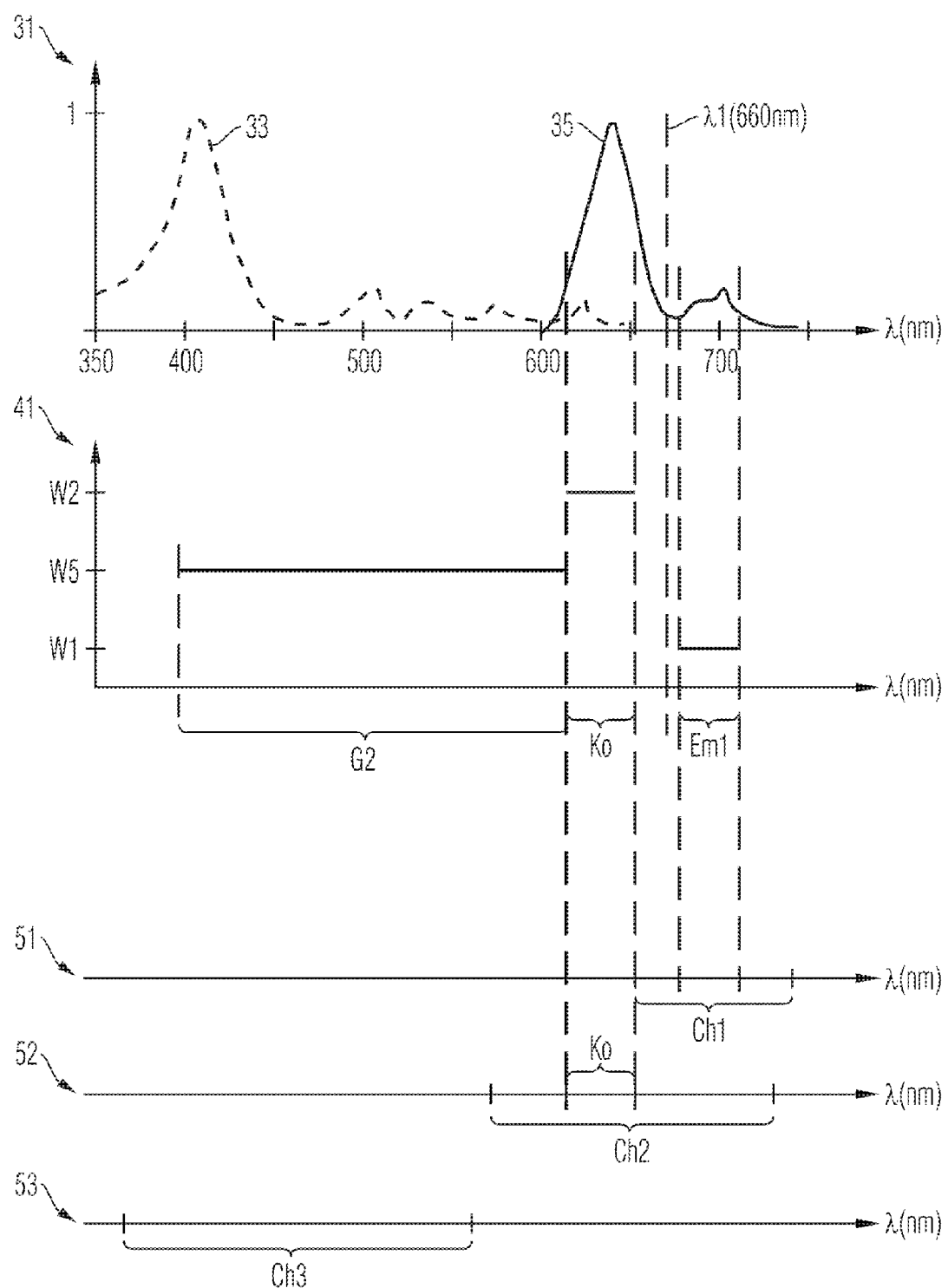
FIG. 8 shows a further exemplary embodiment of a spectral configuration for illumination light and elements of the stereo microscope of FIG. 1.
Figure 9:
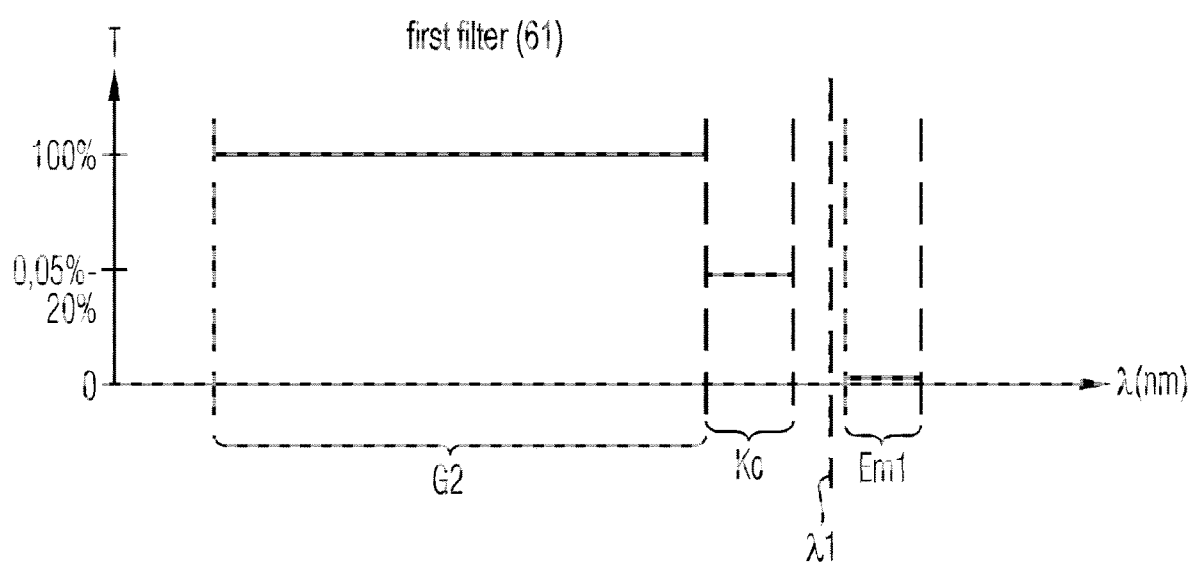
FIG. 9 shows a further exemplary embodiment of a spectral configuration of an optical filter of the stereo microscope of FIG. 1.

FIG. 8 shows an exemplary embodiment of a spectral configuration of the microscopy system. Diagram 31 shows the spectral configuration of the fluorescent dye. Diagram 41 shows the spectral intensity distribution of the illumination light 5.

Diagram 51 shows the spectral configuration of the first detection region of the first fluorescent light image detector 17. Diagram 52 shows the spectral configuration of the second detection region of the first multichannel image detector 19. Diagram 53 shows the spectral configuration of a third detection region of the first multichannel image detector 19.

As illustrated in diagram 41, the illumination light 5 has at least a second intensity W2 in a correction wavelength range Ko and has at most a first intensity W1 in a first emission wavelength range Em1. With this configuration of the illumination light 5, the fluorescent dye is substantially excited in the wavelength range Ko. That means that the correction wavelength range Ko comprises at least a part of the excitation spectrum 33 of the fluorescent dye. In addition, the correction wavelength range Ko is situated between $\lambda Em1L-15$ nm and $\lambda Em1H+150$ nm, wherein the first emission wavelength range Em1 extends from $\lambda Em1L$ to $\lambda Em1H$ and is a first part of the emission spectrum 35 of the fluorescent dye. The first emission wavelength range Em1 and the correction wavelength range Ko do not spectrally overlap.

Again with reference to FIG. 1, the first optical unit 11 is configured to simultaneously image light of the first emission wavelength range Em1 emanating from the object region 7 onto the first detection region of the first fluorescent light image detector 17 and image light of the correction wavelength range Ko emanating from the object region 7 onto the second detection region of the multichannel image detector 19.

As is illustrated in FIG. 8, the first channel Ch1 of the first fluorescent light image detector 17 comprises the first emission wavelength range Em1. Furthermore, the second channel Ch2 of the first multichannel image detector 19 comprises the correction wavelength range Ko.

In accordance with this configuration, the fluorescent dye is excited in the wavelength range Ko. For example, the correction wavelength range Ko comprises the wavelength 630 nm, at which the fluorescent dye PPIX has a local absorption maximum. The correction wavelength range Ko typically comprises a wavelength range from 620 nm to 650 nm, more typically a wavelength range from 610 nm to 660 nm.

The fluorescent dye excited in this manner emits fluorescent light in a secondary maximum around 705 nm. Consequently, the first emission wavelength range Em1 comprises the wavelength 705 nm. The first emission wavelength range typically comprises a wavelength range from 680 nm to 710 nm, more typically from 670 nm to 720 nm.

The microscopy system 1 furthermore comprises the beam splitter 23, which can, for example, be configured as a dichroic beam splitter having a limit wavelength $\lambda 1$ of, for example, 660 nm. Alternatively, the first beam splitter 23 can be a conventional beam splitter, and the microscopy system 1 can furthermore comprise filters, such that the beam splitter 23, in connection with the filters, images light of the emission wavelength range Em1 substantially only onto the first fluorescent light image detector 17 and images light of the correction wavelength range Ko substantially only onto the multichannel image detector 19. The limit wavelength of the first beam splitter 23 is correspondingly situated between the first emission wavelength range Em1 and the correction wavelength range Ko, typically between 600 nm and 700 nm, more typically between 655 nm and 675 nm, even more typically at 660 nm.

Due to this spectral configuration, light of the first emission wavelength range Em1 emanating from the object region 7 is imaged substantially only onto the first detection region and thus detected in the first channel Ch1. The light of the correction wavelength range Ko emanating from the object region 7 is consequently imaged substantially only onto the second detection region and detected in the second channel Ch2.

To produce an overview image with high color fidelity, the illumination light 5 has, in a supplementary wavelength range G2, an average fifth intensity W5 which is lower than the second intensity W2 but higher than the first intensity W1. The average fifth intensity can be, for example, 0.01% to 50% of the second intensity W2, typically 0.05% to 10% of the second intensity W2, more typically 0.1% to 1% of the second intensity W2.

The first optical unit 11 furthermore comprises a first optical filter 61, which is arranged between the first beam splitter 23 and the first multichannel image detector 19. FIG. 9 shows the spectral configuration of the first optical filter 61. An average transmittance of the first optical filter 61 in the correction wavelength range Ko is 0.01% to 50% of an average transmittance of the first optical filter 61 in the supplementary wavelength range G2. An average transmittance of the first optical filter in the first emission wavelength range Em1 can be lower than the average transmittance of the first optical filter 61 in the correction wavelength range Ko by a factor of at least 10. An average transmittance of the first optical filter 61 in the correction wavelength range typically has 0.05% to 10% of the average transmittance of the first optical filter 61 in the supplementary wavelength range G2, more typically 0.1% to 1% of the average transmittance of the first optical filter 61 in the supplementary wavelength range G2. An average transmittance of the first optical filter 61 in the first emission wavelength range Em1 is typically lower than the average transmittance of the first optical filter 61 in the correction wavelength range Ko by at least a factor of 100, more typically 1,000.

The first multichannel image detector 19 can furthermore be configured to detect light of at least one third channel Ch3 in at least one third detection region and convert it into at least one color signal, wherein the at least one third channel Ch3 at most partially overlaps the second channel Ch2 and wherein the at least one third channel Ch3 at least partially comprises the supplementary wavelength range G2. In the exemplary embodiment illustrated in FIG. 8, diagram 53 shows the spectral configuration of the third detection region of the first multichannel image detector 19. The third channel Ch3 at least partially comprises the supplementary wavelength range G2. As in the preceding exemplary embodiments, the first multichannel image detector 19 can be a conventional RGB color camera.

In a development of the microscopy system 1 illustrated in FIG. 1, provided instead of the fluorescent light image detector 17 or 117 is a further multichannel image detector, which is configured to detect at least two different emission wavelength ranges in at least two different channels and to output a separate fluorescent light signal for each channel. For example, this multichannel image detector is configured to detect in one channel a wavelength region around the wavelength 635 nm and to detect in a further channel the wavelength around 705 nm. The fluorescent light signals thus provided can then be used, as described above, to determine the approximation value for the spatial distribution of the concentration of the fluorescent dye in the object region.

In the exemplary embodiments explained above, the first emission wavelength range Em1 can have a width of at least 10 nm, at least 20 nm, at least 50 nm or at least 100 nm. The first correction wavelength range Ko1 can have a width of at least 10 nm, at least 20 nm, at least 50 nm or at least 100 nm. The second correction wavelength range Ko2 can have a width of at least 10 nm, at least 20 nm, at least 50 nm or at least 100 nm.

Furthermore, the second emission wavelength range Em2 can have a width of at least 10 nm, at least 20 nm, at least 50 nm or at least 100 nm. The third correction wavelength range Ko3 can have a width of at least 10 nm, at least 20 nm, at least 50 nm or at least 100 nm. The fourth correction wavelength range Ko4 can have a width of at least 10 nm, at least 20 nm, at least 50 nm or at least 100 nm.

In accordance with a further exemplary embodiment, the first limit wavelength $\lambda 1$ of the first beam splitter 23 and/or the second limit wavelength $\lambda 2$ of the second beam splitter 123 can be located in a wavelength range from 600 nm to 700 nm, in particular at 660 nm.

Arranged between the first beam splitter (23) and the first fluorescent light image detector (17) in accordance with a further exemplary embodiment is a second optical filter having a transmission behaviour which simulates that of the first beam splitter (23). Alternatively, the second optical filter can be configured to transmit substantially only light of the emission wavelength ranges and to suppress light outside the emission wavelength ranges. A further second optical filter can be arranged between the second beam splitter (123) and the second fluorescent light image detector (117).

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A microscopy system for simultaneously recording an overview image and determining a concentration of a fluorescent dye in tissue in an object region, the microscopy system comprising:
   a first detection system, which includes a first fluorescent light image detector;
   the first fluorescent light image detector configured to:
   detect light of a first channel in a first detection region and convert the detected light to a first fluorescent light signal, wherein the first channel includes a first emission wavelength range;
   a first multichannel image detector configured to:
   detect light of a second channel in a second detection region and convert the detected light to a first correction signal, wherein the second channel includes a first correction wavelength range; and
   detect light of a third channel in a third detection region and convert the detected light to a second correction signal, wherein the third channel includes a second correction wavelength range;
   an illumination apparatus configured to produce illumination light and to direct the illumination light onto an object region;
   wherein the illumination light:
   has at most a first intensity in the first emission wavelength range, and
   has at least a second intensity in the first correction wavelength range and in the second correction wavelength range, and
   wherein the first intensity is lower than the second intensity by at least a factor of 2;
   a first optical unit including an objective and a first beam splitter;
   the first optical unit configured to simultaneously:
   image light of the first emission wavelength range emanating from the object region onto the first detection region;
   image light of the first correction wavelength range emanating from the object region onto the second detection region; and
   image light of the second correction wavelength range emanating from the object region onto the third detection region; and
   a controller configured to determine an approximation value for a spatial distribution of the concentration of the fluorescent dye in the object region based on the first fluorescent light signal, the first correction signal, and the second correction signal;
   wherein:
   the first emission wavelength range extends from a first wavelength $\lambda$Em1L to a second wavelength $\lambda$Em1H, wherein the first wavelength $\lambda$Em1L is lower than the second wavelength λEm1H, and is a part of the emission spectrum of the fluorescent dye, the first correction wavelength range is situated between the wavelength λEm1L−150 nm and the wavelength λEm1H+150 nm and does not overlap the first emission wavelength range, and the second correction wavelength range includes a first part of the excitation spectrum of the fluorescent dye.

2. The microscopy system according to claim 1,
wherein the first beam splitter is configured to:
output light of a wavelength that is greater than a first limit wavelength substantially only to the first fluorescent light image detector; and
output light of a wavelength that is smaller than the first limit wavelength substantially only to the first multichannel image detector;
wherein the first limit wavelength is situated between the first emission wavelength range and the first correction wavelength range.

3. The microscopy system according to claim 2,
wherein the first optical unit further comprises a first optical filter arranged between the first beam splitter and the first multichannel image detector,
wherein an average transmittance of the first optical filter in the first correction wavelength range is at least 50%,
wherein an average transmittance of the first optical filter in the second correction wavelength range is at least 50%, and
wherein an average transmittance of the first optical filter has, in the first emission wavelength range, at most a value that is smaller than the average transmittance of the first optical filter in the first correction wavelength range and/or second correction wavelength range by at least a factor of 10.

4. The microscopy system according to claim 3,
wherein the illumination light has at least the second intensity from 450 nm to 550 nm, and
wherein an average transmittance of the first optical filter between the first correction wavelength range and the second correction wavelength range is at least 50%.

5. The microscopy system according to claim 3,
wherein the illumination light has at least the second intensity from 450 nm to 550 nm, and
wherein an average transmittance of the first optical filter has, between the first correction wavelength range and the second correction wavelength range, at most a value that is smaller than the average transmittance of the first optical filter in the first correction wavelength range and/or second correction wavelength range by at least a factor of 10.

6. The microscopy system according to claim 3,
wherein the illumination light has at most the first intensity value between the first correction wavelength range and second correction wavelength range, and
wherein an average transmittance of the first optical filter between the first correction wavelength range and the second correction wavelength range is at least 50%.

7. The microscopy system according to claim 2,
wherein the first multichannel image detector is further configured to detect light of a fourth channel, which in each case at most partially overlaps the second channel and the third channel, in a fourth detection region and convert it to a signal of the fourth channel,
wherein the illumination light has an average fourth intensity in a supplementary wavelength range, which is contained in the fourth channel, wherein the average fourth intensity is 0.01% to 50% of the second intensity, wherein the first intensity is lower than the average fourth intensity by at least a factor of 10; and wherein the first optical unit further comprises a first optical filter arranged between the first beam splitter and the first multichannel image detector, wherein an average transmittance of the first optical filter is, in the first correction wavelength range and the second correction wavelength range, in each case 0.01% to 50% of an average transmittance of the first optical filter in the supplementary wavelength range, and wherein an average transmittance of the first optical filter has, in the first emission wavelength range, at most a value that is smaller than the average transmittance of the first optical filter in the first correction wavelength range and/or second correction wavelength range by at least a factor of 10.

8. The microscopy system according to claim 7, wherein at least one of:
the illumination light has at most the first intensity between the first correction wavelength range and the supplementary wavelength range and between the supplementary wavelength range and the second correction wavelength range, or
an average transmittance of the first optical filter is, between the first correction wavelength range and the supplementary wavelength range and between the supplementary wavelength range and the second correction wavelength range, lower than the average transmittance of the first optical filter in the first correction wavelength range and/or second correction wavelength range in each case by at least a factor of 10.

9. The microscopy system according to claim 1, wherein at least one of:
the emission spectrum of the fluorescent dye includes the wavelength range from 610 nm to 720 nm;
the first emission wavelength range at least partially includes a wavelength range from 620 nm to 660 nm;
the first emission wavelength range at least partially includes a wavelength range from 670 nm to 710 nm;
the second correction wavelength range at least partially includes a wavelength range from 380 nm to 450 nm;
the second correction wavelength range at least partially includes a wavelength range from 600 nm to 650 nm; or
the second and third channels at most partially overlap.

10. The microscopy according to claim 1, further comprising:
a second detection system, which includes a second fluorescent light image detector and a second multichannel image detector,
wherein the second fluorescent light image detector is configured to detect light of a fifth channel in a fifth detection region and convert the detected light to a second fluorescent light signal; wherein the fifth channel includes a second emission wavelength range,
wherein the second multichannel image detector is configured to:
detect light of a sixth channel in a sixth detection region and convert the detected light to a third correction signal; wherein the sixth channel includes a third correction wavelength range, and
detect light of a seventh channel in a seventh detection region and convert the detected light to a fourth correction signal, wherein the seventh channel includes a fourth correction wavelength range;
wherein the illumination light:
has at most the first intensity in the second emission wavelength range, and
has at least the second intensity in the third correction wavelength range and in the fourth correction wavelength range;
a second optical unit, which includes the objective and a second beam splitter; wherein the second optical unit is configured to:
image light of the second emission wavelength range emanating from the object region onto the fifth detection region,
image light of the third correction wavelength range emanating from the object region onto the sixth detection region, and
image light of the fourth correction wavelength range emanating from the object region onto the seventh detection region,
wherein the controller is further configured to:
determine the approximation value for the spatial distribution of the concentration of the fluorescent dye in the object region based on the second fluorescent light signal, the third correction signal, and the fourth correction signal, and
wherein:
the first emission wavelength range and the second emission wavelength range overlap partially or do not overlap;
the second emission wavelength range extends from a third wavelength λEm2L to a fourth wavelength λEm2H, wherein the third wavelength λEm2L is lower than the fourth wavelength λEm2H, and is a second part of the emission spectrum of the fluorescent dye,
the third correction wavelength range is situated between the wavelength AEm2L−150 nm and the wavelength λEm2H+150 nm and does not overlap the second emission wavelength range,
the fourth correction wavelength range includes a second part of the excitation spectrum of the fluorescent dye.

11. The microscopy system according to claim 10, wherein the second beam splitter is configured to:
output light of a wavelength that is greater than a second limit wavelength substantially only to the second fluorescent light image detector, and
output light of a wavelength that is smaller than the second limit wavelength substantially only to the second multichannel image detector,
wherein the second limit wavelength is situated between the second emission wavelength range and the third correction wavelength range.

12. The microscopy system according to claim 1, wherein:
the approximation value is determined using a first function, wherein the first function includes the first fluorescent light signal, the first correction signal, and the second correction signal as arguments, and
the first function includes a term $$I_{FL}^{tot} = A \frac{I_{FL}^{det}}{(I_{Ko1})^\alpha \cdot (I_{Ko2})^\beta},$$

wherein:
$I_{FL}^{tot}$ designates the spatial distribution of the intensity of fluorescent light emitted in the object region,
$I_{FL}^{det}$ designates the first fluorescent light signal,
$I_{Ko1}$ designates the first correction signal,
$I_{Ko2}$ designates the second correction signal,
A designates a first parameter,
α designates a second parameter, and
β designates a third parameter.

13. The microscopy system according to claim 1, wherein at least one of:
the first emission wavelength range,
the first correction wavelength range, or
the second correction wavelength range,
has a width of at least 10 nm.

14. A microscopy system for simultaneously recording an overview image and determining the concentration of a fluorescent dye in tissue in an object region, the microscopy system comprising:
a first multichannel image detector configured to:
detect light of a first channel in a first detection region and convert the detected light to a first fluorescent light signal, wherein the first channel includes a first emission wavelength range,
detect light of a second channel in a second detection region and convert the detected light to a first correction signal, wherein the second channel includes a first correction wavelength range,
detect light of a third channel in a third detection region and convert the detected light to a second correction signal, wherein the third channel includes a second correction wavelength range,
wherein the first, second, and third channels substantially do not spectrally overlap;
an illumination apparatus configured to produce illumination light and to direct the illumination light onto the object region, wherein the illumination light:
has at most a first intensity in the first emission wavelength range, and
has at least a second intensity in the first correction wavelength range and in the second correction wavelength range,
wherein the first intensity is lower than the second intensity by at least a factor of 2;
a first optical unit having an objective and configured to simultaneously:
image light of the first emission wavelength range emanating from the object region onto the first detection region,
image light of the first correction wavelength range emanating from the object region onto the second detection region, and
image light of the second correction wavelength range emanating from the object region onto the third detection region;
a controller configured to determine an approximation value for a spatial distribution of a concentration of the fluorescent dye in the object region based on the first fluorescent light signal, the first correction signal, and the second correction signal; wherein:
the first emission wavelength range extends from a first wavelength λEm1L to a second wavelength λEm1H, wherein the first wavelength λEm1L is lower than the second wavelength λEm1H, and is a part of the emission spectrum of the fluorescent dye, the first correction wavelength range is situated between the wavelength $\lambda Em1L-150$ nm and the wavelength $\lambda Em1H+150$ nm and does not overlap the first emission wavelength range, and the second correction wavelength range includes a first part of the excitation spectrum of the fluorescent dye.

15. The microscopy system according to claim 14, wherein at least one of:

the first emission wavelength range at least partially includes a wavelength range from 610 nm to 650 nm, the first correction wavelength range at least partially includes a wavelength range from 560 nm to 610 nm, or the second correction wavelength range at least partially includes a wavelength range from 390 nm to 450 nm.

16. The microscopy system according to claim 14, wherein at least one of:

the first emission wavelength range at least partially includes a wavelength range from 670 nm to 710 nm, the first correction wavelength range at least partially includes a wavelength range from 600 nm to 660 nm, or the second correction wavelength range at least partially includes a wavelength range from 390 nm to 450 nm.

17. The microscopy system according to claim 14, wherein:

the multichannel image detector is further configured to detect light of a fourth channel in a fourth detection region and convert the detected light to a second fluorescent light signal, the fourth channel includes a second emission wavelength range, the first, second, third, and fourth channels substantially do not spectrally overlap, the illumination light has at most the first intensity in the second emission wavelength range, the first optical unit is further configured to simultaneously image light of the second emission wavelength range emanating from the object region onto the fourth detection region, the controller is further configured to determine the approximation value for the spatial distribution of the concentration of the fluorescent dye in the object region based on the second fluorescent light signal, and the second emission wavelength range is a second part of the emission spectrum of the fluorescent dye, and the first and second emission wavelength ranges do not overlap.

18. A microscopy system for simultaneously recording an overview image and determining the concentration of a fluorescent dye in tissue in an object region, the microscopy system comprising:

a first detection system having a first fluorescent light image detector and a first multichannel image detector, wherein the first fluorescent light image detector is configured to detect light of a first channel in a first detection region and convert the detected light to a first fluorescent light signal, wherein the first channel includes a first emission wavelength range, wherein the first multichannel image detector is configured to detect light of a second channel in a second detection region and convert the detected light to a correction signal, wherein the second channel comprises a correction wavelength range;

an illumination apparatus configured to produce illumination light and to direct the illumination light onto the object region, wherein the illumination light has at most a first intensity in the first emission wavelength range, and has at least a second intensity in the correction wavelength range, wherein the first intensity is lower than the second intensity by at least a factor of 2;

a first optical unit including an objective and a first beam splitter, wherein the first optical unit is configured to simultaneously:

image light of the first emission wavelength range emanating from the object region onto the first detection region; and image light of the correction wavelength range emanating from the object region onto the second detection region; and a controller configured to determine an approximation value for the spatial distribution of the concentration of the fluorescent dye in the object region using the first fluorescent light signal and the correction signal; wherein:

the first emission wavelength range extends from a first wavelength $\lambda Em1L$ to a second wavelength $\lambda Em1H$, wherein the first wavelength $\lambda Em1L$ is lower than the second wavelength $\lambda Em1H$, and is a part of the emission spectrum of the fluorescent dye, and the first correction wavelength range is situated between the wavelength $\lambda Em1L-150$ nm and the wavelength $\lambda Em1H+150$ nm, does not overlap the first emission wavelength range, and includes a first part of the excitation spectrum of the fluorescent dye.

19. The microscopy system according to claim 18, wherein the first beam splitter is configured to:

output light of a wavelength that is greater than a first limit wavelength substantially only to the first fluorescent light image detector, and output light of a wavelength that is smaller than the first limit wavelength substantially only to the first multichannel image detector, wherein the first limit wavelength is situated between the first emission wavelength range and the correction wavelength range.

20. The microscopy system according to claim 19, wherein the illumination light has an average fifth intensity in a supplementary wavelength range, wherein the average fifth intensity is 0.01% to 50% of the second intensity, wherein the first intensity is lower than the average fifth intensity by at least a factor of 10, and wherein the first optical unit further comprises:

a first optical filter arranged between the first beam splitter and the first multichannel image detector, wherein an average transmittance of the first optical filter is, in the correction wavelength range, 0.01% to 50% of an average transmittance of the first optical filter in the supplementary wavelength range, and wherein an average transmittance of the first optical filter is, in the first emission wavelength range, lower than the average transmittance of the first optical filter in the correction wavelength range by at least a factor of 10.

21. The microscopy system according to claim 20, wherein at least one of:
- the supplementary wavelength range has a width of at least 50 nm;
- the supplementary wavelength range includes only wavelengths that are smaller than the first limit wavelength;
- the supplementary wavelength range at least partially includes the wavelength range from 500 nm to 600 nm; or
- the supplementary wavelength range and the correction wavelength range do not overlap.

22. The microscopy system according to claim 20, wherein the first multichannel image detector is further configured to detect light of at least one third channel in at least one third detection region and convert the detected light into at least one color signal,
wherein the at least one third channel at most partially overlaps the second channel, and
wherein the at least one third channel at least partially includes the supplementary wavelength range.

23. The microscopy system according to claim 18, wherein the approximation value is determined with a second function, wherein the second function has the first fluorescent light signal and the correction signal as arguments,
wherein the second function includes as a term $$I_{FL}^{tot} = B \frac{I_{FL}^{det}}{(I_{Ko})^{\gamma}},$$

wherein:
$I_{FL}^{tot}$ designates the spatial distribution of the intensity of fluorescent light emitted in the object region,
$I_{FL}^{det}$ designates the first fluorescent light signal,
$I_{Ko}$ designates the correction signal,
B designates a fourth parameter, and
$\gamma$ designates a fifth parameter.

* * * * *

UNITED STATES PATENT AND TRADEMARK OFFICE
CERTIFICATE OF CORRECTION

PATENT NO. : 11,036,039 B2
APPLICATION NO. : 15/977792
DATED : June 15, 2021
INVENTOR(S) : Marco Wilzbach and Christoph Hauger Page 1 of 1

It is certified that error appears in the above-identified patent and that said Letters Patent is hereby corrected as shown below:

In the Specification

<u>In Column 1:</u>

Line 64: Replace " $I_{FL}^{total} = A \frac{I_{FL}^{det}}{(I_{Ko1})^\alpha \cdot (I_{Ko2})^\beta}$ ," with " $I_{FL}^{tot} = A \frac{I_{FL}^{det}}{\left(I_{Ko1}\right)^\alpha \cdot \left(I_{Ko2}\right)^\beta}$ ,"

In the Claims

<u>In Column 20, Claim 10:</u>
Line 50: Replace "microscopy" with "microscopy system"

<u>In Column 21, Claim 10:</u>
Line 38: Replace "AEm2L" with "λEm2L"

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*